United States Patent
Knapp et al.

[11] Patent Number: 5,824,081
[45] Date of Patent: Oct. 20, 1998

[54] HYDRAULIC FOAM TISSUE IMPLANT

[75] Inventors: Terry R. Knapp, Neuchatel, Switzerland; Winston A. Andrews, Danville, Calif.; Pierre Comte, Neuchâtel, Switzerland

[73] Assignee: LipoMatrix Incorporated, Virgin Islands (Br.)

[21] Appl. No.: 710,180

[22] Filed: Sep. 13, 1996

[51] Int. Cl.⁶ .................................................. A61F 2/02
[52] U.S. Cl. ............................................. 623/11; 623/8
[58] Field of Search ................... 623/1, 7, 8, 11, 623/12, 16, 66, 901

[56] References Cited

U.S. PATENT DOCUMENTS

| | | |
|---|---|---|
| 2,542,619 | 2/1951 | Bernhardt . |
| 2,842,775 | 7/1958 | Pangman . |
| 3,189,921 | 6/1965 | Pangman ..................................... 623/8 |
| 3,366,975 | 2/1968 | Pangman ..................................... 623/8 |
| 3,559,214 | 2/1971 | Pangman . |
| 3,683,424 | 8/1972 | Pangman . |
| 4,298,998 | 11/1981 | Naficy . |
| 4,428,082 | 1/1984 | Naficy . |
| 4,507,810 | 4/1985 | Bartholdson . |
| 4,517,326 | 5/1985 | Cordts et al. . |
| 4,531,244 | 7/1985 | Hamas . |
| 4,636,213 | 1/1987 | Pakiam . |
| 4,650,487 | 3/1987 | Chaglassian ................................. 623/8 |
| 4,773,909 | 9/1988 | Chaglassiau . |
| 4,790,848 | 12/1988 | Cronin . |
| 4,863,470 | 9/1989 | Carter ........................................... 623/8 |
| 4,955,907 | 9/1990 | Ledergerber ................................. 623/8 |
| 4,995,882 | 2/1991 | Destouet et al. ............................. 623/8 |
| 5,092,882 | 3/1992 | Lynn et al. . |
| 5,236,454 | 8/1993 | Miller . |
| 5,246,454 | 9/1993 | Peterson . |
| 5,282,856 | 2/1994 | Ledergerber ................................. 623/8 |
| 5,358,521 | 10/1994 | Shane . |
| 5,383,929 | 1/1995 | Ledergerber . |
| 5,437,824 | 8/1995 | Carlisle et al. ............................. 264/50 |
| 5,653,755 | 8/1997 | Ledergerber ................................. 623/8 |
| 5,658,330 | 8/1997 | Carlisle et al. ............................. 623/8 |

*Primary Examiner*—Mickey Yu
*Assistant Examiner*—Francis K. Cuddihy
*Attorney, Agent, or Firm*—Howell & Haferkamp, L.C.

[57] ABSTRACT

The invention relates to a tissue implant having visco-elastic characteristics which simulate the natural tissue that is intended to be augmented or replaced. The implant is comprised of a shell or envelope enclosing a compound foam body and a fluid filler material. Both the foam body and the fluid filler are should be biocompatible and preferably are substantially radiolucent using standard mammographic materials and protocols. The compound foam body is of elastomeric cellular foam materials. Intercellular communication of the fluid filler provides a hydraulic mechanism for imparting shape and tissue-like consistency to the implant. The compound foam body has multiple regions, each region having a different cellular density, for simulating the tactile characteristics of the natural tissue that the implant is intended to augment or replace. The implant may also have a cavity in the compound foam body configured for providing a hydraulic reservoir for the fluid filler. The resiliency of the compound foam body permits realistic elastic deformation, in response to external pressure, and "rebound" following such deformation.

27 Claims, 1 Drawing Sheet

HYDRAULIC FOAM TISSUE IMPLANT

BACKGROUND OF THE INVENTION

This invention relates to a tissue implant having viscoelastic characteristics which simulate the natural tissue that is intended to be augmented or replaced. The apparatus and method of the present invention may be used in various applications relating to soft tissue implants such as breast, calf, pectoral, and buttock implants and can also be used to simulate bony contour and feel.

Breast prostheses, in particular, are well-known in the art and generally include a shell or envelope which is filled with a high viscosity fluid or gel which desirably is used to enlarge the breast yet retain its normal appearance, movement, feel, and other cosmetic characteristics. Most of these implants consist of a single compartment filled with the fluid. Several implants have multiple, grossly septated fluid-filled compartments for preventing excessive movement and maintaining a natural shape.

Until recently, the predominant breast implant had been a single-compartment silicone envelope filled with a silicone gel. However, health risks caused by migration of the silicone gel from within the shell, breakage of the shell, or other introduction of the silicone gel into the body, have prompted the withdrawal of this implant from the market. More recently, other high viscosity fluid-fillers have been used which are more biocompatible than silicone gel. In addition to the serious health concerns, another problem with implants containing high viscosity fluid-fillers is a lack of realistic elastic shape memory or "rebound" following deformation of the implant. A further problem with prior art tissue implants that are comprised of a shell or envelope filled only with a fluid or gel filler is a tendency of the shell over time to wrinkle or ripple under gravity-induced stresses.

Still another problem with prior art tissue implants that are filled with highly viscous fluids is a lack of radiolucency as compared to natural tissues surrounding the implant. Consequently, significant portions of the glandular tissue in the breast are obscured during mammography procedures. To overcome this problem, tissue implants have been developed which are constructed of radiolucent materials. The assignee of the present invention holds certain rights under U.S. Pat. No. 4,995,882, the disclosure of which is incorporated herein by reference, which discloses a useful and valuable invention utilizing a fill material which is radiolucent using standard mammographic procedures and protocols. This prior patent discloses and claims a breast implant comprised of a silicone shell filled with a radiolucent fill material such as peanut oil, sunflower seed oil, or another suitable fluid with the same atomic number as breast tissue, i.e., Z=5.5 to 6.5. The assignee of the present invention is also the owner of pending application Ser. No. 08/250,339, filed May 27, 1994, the disclosure of which is incorporated herein by reference, which discloses a breast implant wherein both the fill material and the shell are made of a material which is substantially radiolucent using the standards for judging radiolucency as explained in both of these prior filings, i.e., using standard mammographic protocols and procedures.

The inventors herein are aware of U.S. Pat. No. 3,683,424 of Pangman which discloses a breast implant comprising an elastic shell containing a cellular foam core and a quantity of liquid in the cells of the core. The flow of liquid between cells of the foam core is also disclosed. The disclosure states that movement of fluid throughout the foam core would be facilitated by increasing the sizes of the pores. However, as the size of pores in the foam core are increased, the foam will become softer and more susceptible to deformation. It may therefore be desired to have a relatively small pore size in order to maintain the intended shape and feel of the implant.

This patent does not disclose the use of a compound foam core; that is, a foam core having multiple regions of different pore size or different cellular density. Instead, the foam core used in this patent is apparently a unitary core having a substantially uniform pore size and cellular density throughout. Therefore, to overcome the problem of limited fluid movement in foam cores having small pore sizes, this patent further discloses a variant embodiment of the implant which includes a number of radial slits cut into the periphery of the foam core. The slits may extend toward the center of the core and terminate just beneath the exterior surface of the core or they may extend completely through the foam core. These slits are intended to provide a controlled increase and the ease of movement of liquid within the core.

In constructing the implant disclosed in the Pangman patent, one is limited to the use of a one-piece foam core having a uniform pore size and cellular density throughout. In order to obtain a desired feel and response to external pressures, one must resort to incorporating the slits referred to above for increasing fluid flow throughout the implant. Therefore, in attempting to construct an implant that closely simulates the tactile characteristics of the natural tissue that is to be augmented or replaced, one's options are limited when following the teachings of the Pangman patent. The limitations of this prior art patent are recognized and improved upon in the present invention.

The inventors herein are also aware of U.S. Pat. No. 4,507,810 of Bartholdson which discloses a breast implant comprised of a shell that is completely filled with a plurality of discrete, irregularly-shaped sacs which are attached to one another. This implant is at least partially filled with a fluid and the sacs may have passageways for providing fluid communication between sacs. The sacs are attached to one another and to the shell for preventing excessive movement of the implant.

By using this system of interconnected sacs which permit fluid communication between the sacs, the Bartholdson patent is aimed at providing a breast implant with a shape and feel that resembles the body's own tissue. However, this patent does not provide the option of using a compound core for better simulating natural tissue as described above. Although irregularly-shaped sacs are disclosed, this patent does not disclose a core with multiple regions having different pore sizes or different cellular densities. Therefore, as with the Pangman patent discussed above, in attempting to construct an implant that closely simulates the tactile characteristics of the natural tissue that is to be augmented or replaced, one's options are limited according to the teachings of the Bartholdson patent.

Construction of an implant according to the teachings of the Bartholdson patent would be rather complex and cumbersome since the individual sacs must be attached to one another and to the shell. The patent suggests ultrasonic welding, gluing or other curing techniques for attaching the sacs to one another and to the shell. The patent does not disclose or suggest a cellular core comprised of a material, such as opened celled foam rubber or foam plastic, where the sacs or cells are, by nature, attached to one another.

Construction of an implant according to the Bartholdson patent is further complicated since, as disclosed, the individual sacs must only be connected to one another at "junction points" so that the passageways in each of the sacs are properly aligned to permit fluid communication between sacs. The limitations and complexities of this prior art implant are recognized and improved upon in the present invention.

SUMMARY OF THE INVENTION

The present invention comprises a tissue implant constructed of biocompatible materials which are also radiolucent. The implant is configured for having visco-elastic characteristics which closely simulate the natural tissue which is intended to be augmented or replaced.

Accordingly, it is an object of this invention to provide a tissue implant with visco-elastic properties that closely mimic natural tissue consistency and feel. A related object of the present invention is to provide a tissue implant with realistic "rebound" from elastic deformation, i.e., good elastic "shape memory." In furtherance of these objectives, this invention aims to provide the option of constructing an implant with a compound foam core comprising a number of regions having different pore sizes or cellular densities and, therefore, different tactile characteristics.

Another object of this invention is to provide a tissue implant with radiolucency substantially equivalent to surrounding tissues for permitting unobstructed x-ray diagnosis. A further object is to provide an implant with exceptional fatigue resistance and rupture resistance in comparison with single-compartment or grossly septated implants filled only with fluid or gel. Yet another object is to provide an implant which minimizes or eliminates gravity-induced wrinkling and rippling of the shell as is observed in single-compartment or grossly septated implants filled only with fluid or gel.

The tissue implant of the present invention comprises a shell or envelope enclosing a compound foam body and a fluid filler material. Both the foam body and the fluid filler are biocompatible and also substantially radiolucent using standard mammographic procedures and protocols. The foam body is made of a cellular foam material having a multiplicity of cells which divide the fluid filled volume of the shell. The cellular foam material is preferably an elastomeric polymer foam but may be a non-elastomeric polymer foam. The foam body has an "open-cell" structure which permits intercellular communication of the fluid filler. The interconnected cells allow the passage of fluid from cell to cell for creating a hydraulic cushioning effect upon deformation of the implant. Thus, the intercellular fluid communication provides a hydraulic mechanism for imparting realistic shape and tissue-like consistency to the implant.

The foam body is a compound foam body comprised of multiple regions, each region having a different cellular density. The cellular density of a region refers to the number of cells per unit of volume in that region. The cellular density of a region is therefore dependent on the size of the cells in the region. The regions may consist of different portions of a single foam piece or may be several adjacent, but discrete foam pieces. In embodiments where the regions consist of several adjacent but discrete pieces, the pieces may be attached to one another or unattached. Additionally, the pieces may or may not be attached to the shell.

The tissue implant of the present invention may also include one or more cavities in the compound foam body configured for providing hydraulic reservoirs for the fluid filler. The cavities are substantially larger than any of the cells and may be located completely within one of the regions or pieces or may be located between two or more regions or pieces.

As stated above, the compound foam body is of an elastomeric foam material, the resiliency of which enables the body to elastically deform in response to external pressure and to regain its original configuration, or "rebound," following such deformation. When an area of the implant is elastically deformed by external pressure, the intercellular passages allow the fluid filler to flow from cells in the area of such deformation into nearby cells via the passages. After the external pressures are removed, the passages permit the fluid filler to equilibrate by returning to cells in the area of the deformation. Due to its resiliency, deformation of the implant from external pressure is only temporary. The degree and duration of the elastic deformation and "rebound" will depend upon the cellular density of the foam body and the capacity of the intercellular passages in the area undergoing deformation.

As discussed above, and as further set forth in U.S. Pat. No. 4,995,882 and pending U.S. patent application Ser. No. 08/250,339, the disclosures of which have been incorporated herein by reference, the fluid filler and the shell of the implant are made of a biocompatible material which is substantially radiolucent under standard mammographic protocols and intensities. In the present invention, the compound foam body is also at least partially made of a biocompatible material which is substantially radiolucent under standard mammographic protocols and intensities.

The hydraulic foam tissue implant of the present invention provides a resiliency, shape and consistency impossible to achieve with a single compartment or grossly septated implant. The concept of the cellular foam containing implant is to reduce a single compartment or a few compartments to a true multicellular structure with thousands to millions of compartments. Moreover, the concept of a compound foam core comprised of multiple regions having different cellular densities is to better simulate the non-homogeneous, multicellular tissue that the implant aims to augment or replace. The concept of a compound core provides options for customizing soft tissue implants that are not provided with one-piece, single-density, foam cored implants. The present invention does not suffer the limitations and complexities of the Pangman and Bartholdson patents, discussed above, and therefore provides greater flexibility in constructing customized soft tissue implants which succeed in simulating the natural tissues being augmented or replaced.

Further objects and features of the present invention will be in part apparent and in part pointed out hereinafter.

DESCRIPTION OF THE PREFERRED EMBODIMENTS

Figure 1:
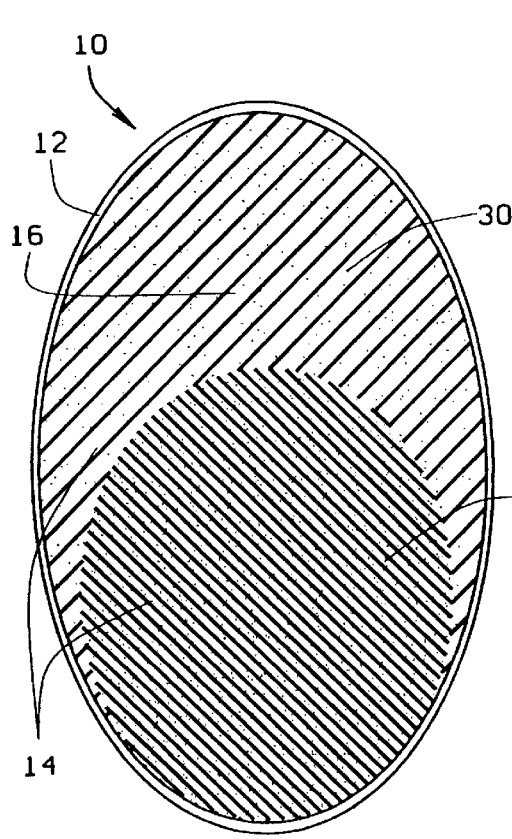
FIG. 1 is a coronal cut-away view of the hydraulic foam tissue implant of the present invention.

Referring to FIG. 1, the hydraulic foam tissue implant of the present invention is shown generally as 10. The implant 10 comprises a shell 12 enclosing a compound foam body 14 and a fluid filler material 16, depicted as the space within the shell 12. The shell 12 may be constructed of an elastomeric or non-elastomeric material and may have a smooth or textured surface. The shell material should be biocompatible with the host tissue and chemically stable with the fluid filler 16 and foam body 14. Preferably, the shell 12 is of a silicone elastomer material. Other shell materials may include ePTFE, thermoset and thermoplastic polymers, and natural protein polymers.

Both the foam body 14 and the fluid filler 16 are also biocompatible with the host tissue. The host is therefore protected in the event of a shell rupture. Any fluid filler 16 that migrates out of the shell 12 or leaks out in the event of a shell rupture will be metabolized and excreted. The shell 12, the fluid filler 16, and the foam body 14 are also substantially radiolucent using standard mammographic procedures and protocols, as will be discussed further.

Figure 3:
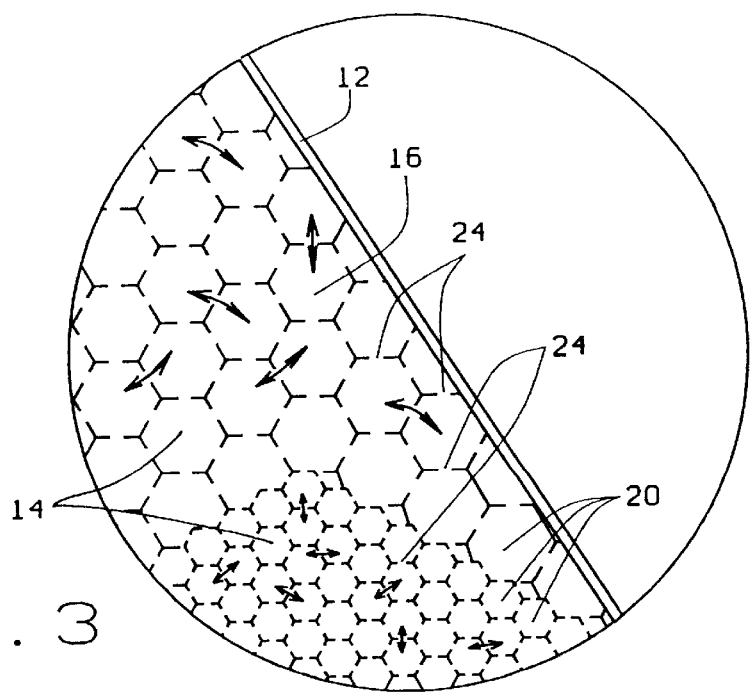
FIG. 3 is a detail view showing more features of the sagittal cut-away view.

Referring now to the details in FIG. 3, the foam body 14 is constructed of a cellular foam material having a multiplicity of cells 20 which divide the fluid filled volume of the shell 12 into thousands or millions of compartments. The cellular foam material is a thermoset or thermoplastic polymer. Preferably, the cellular foam material has elastomeric qualities but may be of a non-elastomeric polymer foam. The shape of the foam body 14 determines the basic shape of the implant 10 since the cellular foam material maintains a substantially full shape with or without the fluid filler 16. The particular material or materials chosen for constructing the foam body 14 will depend, at least in part, on the density or hardness of the tissue to be simulated.

The foam body 14 has an "open-cell" structure, the cells being interconnected with one another by passages 24 that permit intercellular communication of the fluid filler 16. The arrows in FIG. 3 are used for purposes of illustrating the intercellular communication of the fluid filler 16. The passages 24 interconnecting the cells 20 allow the flow of fluid filler 16 from cell to cell for creating a hydraulic cushioning effect upon deformation of the implant 10. The hydraulic cushioning effect created by intercellular fluid communication helps to impart realistic shape and tissue-like consistency to the implant 10. The fluid filler 16 may be introduced at the time of manufacture or may be introduced later through a fill valve, creating an inflatable or adjustable implant.

The foam body is a compound foam body comprised of multiple regions, a first region 30 and a second region 32 different than the first region 30, each having a different cellular density for simulating varying density patterns of the natural tissue that is to be augmented or replaced. The compound foam body 14 may also comprise one or more cavities 40 which are further described below. The number, size, and cellular density of the regions defining the foam body will depend on the particular requirements of the natural tissue which is to be simulated.

For example, an area of very soft resilient "tissue," such as fatty tissue, may demand a foam with large cells 20 and high capacity passages 24. Similarly, an area of more dense "tissue," such as glandular tissue, may demand a foam that has smaller cells 20 with passages 24 of lower fluid flow capacity. Regions of very high density may be required for simulating cartilage or bone.

The cellular density of a region 30, 32 refers to the number of cells 20 per unit of volume in that region 30, 32. The cellular density of a region 30, 32 is therefore dependent on the size of the cells 20 in the region 30, 32. The regions 30, 32 may comprise different portions of a unitary foam piece or may comprise several discrete foam pieces positioned adjacent to one another. In embodiments where the regions comprise several adjacent but discrete pieces, the pieces may be attached to one another or may be unattached. Additionally, the pieces may or may not be attached to the shell. A region or piece, depending on the particular embodiment of the foam body 14, may have a uniform cellular density or may have a cellular density that varies throughout the region 30, 32, i.e., a cellular density gradient. In the case of an embodiment which includes one or more regions 30, 32 having a cellular density gradient, the regions 30, 32 will have different average cellular densities. The average cellular density of a region 30, 32 is defined by an arithmetic average of the cells 20 per unit of volume in that region 30, 32.

Figure 2:
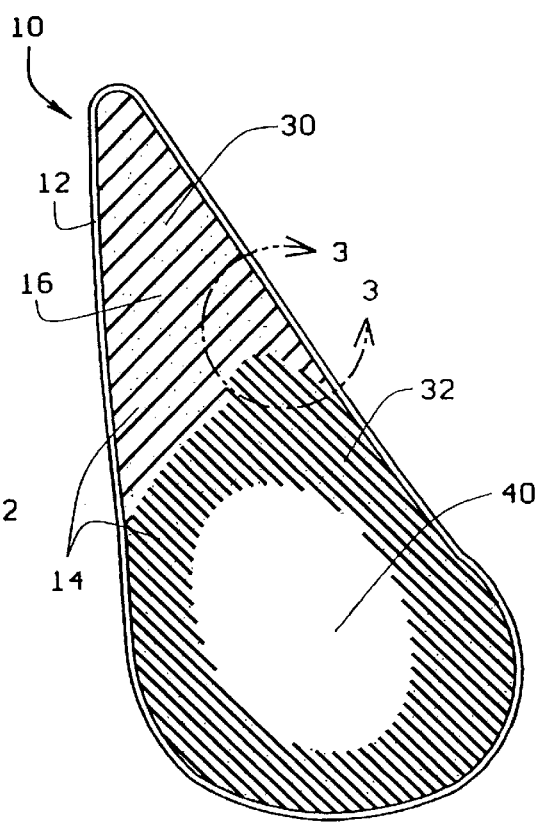
FIG. 2 is a sagittal cut-away view of the hydraulic foam tissue implant.

Referring now to FIG. 2, the preferred embodiment of the hydraulic foam tissue implant of the present invention also comprises a cavity 40 in the compound foam body 14 configured for providing a hydraulic reservoir for the fluid filler 16. The cavity 40 is substantially larger than any of the cells 20 and may be located partially or completely within one of the regions or pieces 30, 32 or may be located between two or more regions or pieces 30, 32. Depending on the visco-elastic properties of the host tissue which is to be simulated, alternate embodiments may have more than one hydraulic reservoir 40. Still other embodiments may require no hydraulic reservoirs of this kind.

As stated above, the compound foam body 14 is constructed of an elastomeric foam material, the resiliency of which enables the body 14 to elastically deform in response to external pressure. The resiliency of the foam body 14 also permits it to regain its original configuration, or "rebound," following such deformation. The intercellular passages 24 in the foam body 14 are configured such that, when an area of the implant is elastically deformed by external pressure, the passages 24 allow the fluid filler 16 to flow from cells 20 in the area of such deformation into other cells, or into cavities 40, via the passages 24. After the external pressures are removed, the passages 24 permit the fluid filler 16 to equilibrate by returning to cells 20 which were evacuated. Due to its resiliency, deformation of the implant 10 from external pressure is only temporary. The degree and duration of the elastic deformation and "rebound" will depend on, among other things, the cellular density of the compound foam body 14 and the capacity of the intercellular passages 24 in the area undergoing deformation.

As further set forth in U.S. Pat. No. 4,995,882 and U.S. patent application Ser. No. 08/250,339, the fluid filler 16 and the shell 12 of the implant are made of a material which is substantially radiolucent under standard mammographic protocols and intensities.

The shell 12 may be constructed of linear aliphatic polyether urethane; linear aliphatic polyester urethane; cyclic aliphatic polyether urethane; cyclic aliphatic polyester urethane; aromatic polyether urethane; aromatic polyester urethane; polybutylene; polypropylene; crosslinked olefinic elastomers; styrene-ethylene/butylene-styrene block copolymer; or any other biocompatible material which is substantially radiolucent under standard mammographic protocols and intensities. Likewise, the fluid filler 16 may be made of a biocompatible triglyceride, serum, saline solution, or another biocompatible material which is substantially radiolucent under standard mammographic protocols and intensities.

In the preferred embodiment of the present invention, the compound foam body 14 is also made of a material which is substantially radiolucent under standard mammographic protocols and intensities. The compound foam body 14 may be constructed of styrene-ethylene-butylene-styrene copolymer; polyethylene; polyurethane; and polytetrafluoroethylene; or another biocompatible material which is substantially radiolucent under standard mammographic protocols and intensities.

The method used for constructing the soft tissue implant of the present invention 10 requires construction of a flexible shell 12 and a compound foam body 14 to desired dimensions. Before constructing the compound foam body 14, it is necessary to determine the tissue characteristics, e.g., size, shape, density patterns, etc., of the tissue to be augmented or replaced so that the resulting implant 10 will have characteristics which closely simulate the feel and consistency of the natural tissue. Therefore, the tactile characteristics of the natural tissue to be augmented or replaced must be must be documented or "mapped."

Tissue characteristics may be "mapped" generically or by a customized analysis. Generic "mapping" of tissue characteristics relies on general knowledge of the tissue type and distribution to be simulated by the implant. For example, a series of breast implants of like configuration could be manufactured using breast tissue characteristics which are generally known to those skilled in the art. Particularly, it is generally known that the tissue to be simulated by a breast implant is comprised of a combination of soft, fatty tissue which overlies more dense, centrally and inferiorally located glandular tissue.

"Mapping" tissue for custom implant manufacture may be accomplished by defining a template of the implant to be produced using computer surface rendering techniques or, alternatively, the production of moulage by the surgeon. Detailed data for the tissues to be simulated by a custom manufactured implant may be obtained using ultrasound, CT scan or magnetic resonance imaging (MRI) for providing a three dimensional source of information relative to the various tissues involved and their relative proportion and position. Alternatively, the surgeon ordering such a prosthesis may simply indicate the areas of tissue type to be simulated on a diagram.

Based on these determinations, a compound foam body 14 is constructed to match what was "mapped" so that the resulting implant will provide the desired shape indensity to simulate fat, muscle, glandular tissue, bone, cartilage, etc. In order to match the "feel" of a specific tissue site, the density of the foam, chemical composition of the foam, viscosity of the fluid filler, and composition and thickness of the shell can be varied. As discussed above, the number, size, and density patterns of regions or pieces 30, 32 defining the compound foam body 14 will depend on the particular requirements of the natural tissue which is to be simulated. Likewise, the number, configuration, and location of hydraulic reservoirs 40 included in the compound foam body 14, if any, will depend on the visco-elastic properties of the host tissue which is to be simulated.

The completed compound foam body 14 is inserted in the flexible shell 12. The method also includes the steps of filling the shell 12 with a fluid filler 16 and removing air from the cells 20 of the compound foam body 14. In the preferred method, filling the shell 12 with the fluid filler 16 and removing air from the cells 20 of the foam body 14 is accomplished simultaneously. Filling the implant 10 with the fluid filler 16 may be accomplished at the time of manufacture or by the end user, provided with a filling system by the manufacturer.

Filling the implant with the fluid filler may be performed by installation of an active valve or other fill port into the shell of the implant. Initial evacuation of trapped air may be accomplished by simple suction. The implant is partially filled with the fluid filler and then rotated to place the fill port at an uppermost portion of the implant. Then, by gentle squeezing, the trapped air rises to the fill port and can be released from the implant by suction. Filling may then be completed at the point of manufacture. Alternatively, the implant may be packaged partially collapsed with final fluid inflation to be completed by the surgeon at the time of implant insertion.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense. The invention therefore shall be limited solely by the scope of the claims set forth below.

What is claimed is:

1. A tissue implant comprising a flexible shell, a fluid filler within the shell, a compound foam body disposed within said shell, the compound foam body comprising a distinct first foam region having a substantially uniform first cellular density throughout said first foam region, and a distinct second foam region having a substantially uniform second cellular density throughout said second foam region, the second cellular density being different than the first cellular density, and a cavity in said compound foam body adapted to provide a hydraulic reservoir for the fluid filler, said cavity being substantially larger than any cell.

2. The tissue implant of claim 1 wherein said foam body is of a resilient material which is elastically deformable, the resiliency of said body enabling said body to deform in response to external pressure and to regain an original configuration following such deformation.

3. The tissue implant of claim 2 wherein the first foam region has a first multiplicity of cells and the second foam region has a second multiplicity of cells, the first and second multiplicity of cells being connected to one another by passages to thereby allow intercellular communication of the fluid filler throughout the first foam region, the second foam region and said cavity.

4. The tissue implant of claim 3 wherein, when an area of the implant is deformed by external pressure, the passages are configured to allow said fluid filler to flow from cells in the area of such deformation into other cells and into the cavity.

5. The tissue implant of claim 4 wherein, following the removal of such external pressure, the passages are configured to permit said fluid filler to equilibrate by returning to cells in the area where the deformation occurred.

6. The tissue implant of claim 1 wherein said fluid filler and said foam body are of materials which are substantially radiolucent under standard mammographic protocols and intensities.

7. A method of making a tissue implant, the method comprising the steps of providing a flexible shell, providing a compound foam body comprising a distinct first foam region having a substantially uniform first cellular density throughout said first foam region, and a distinct second foam region having a substantially uniform second cellular density throughout said second foam region, the second cellular density being different than the first cellular density, and inserting the compound foam body in the flexible shell.

8. The method of claim 7 further comprising the step of replacing air in cells of the compound foam body by filling the shell with a fluid filler.

9. The method of claim 7 wherein the step of providing a compound foam body includes providing a compound foam body comprised of two separate foam pieces.

10. The method of claim 7 wherein the step of providing a compound foam body includes providing a compound foam body comprised of a single monolithic foam piece.

11. A tissue implant comprising a flexible shell enclosing a volume, a fluid filler within the shell, and a compound foam body disposed within the shell, the compound foam body comprising a distinct first foam region having a substantially uniform first cellular density throughout said first foam region, and a distinct second foam region having a substantially uniform second cellular density throughout said second foam region, the second cellular density being different than the first cellular density, the first foam region having a first multiplicity of cells and the second foam region having a second multiplicity of cells.

12. The tissue implant of claim 11 wherein the first multiplicity of cells are connected to one another by passages to thereby allow intercellular communication of the fluid filler throughout the first foam region, and wherein the second multiplicity of cells are connected to one another by passages to thereby allow intercellular communication of the fluid filler throughout the second foam region.

13. The tissue implant of claim 12 further comprising a cavity in said foam body adapted to provide a hydraulic reservoir for the fluid filler, said cavity being substantially larger than any cell.

14. The tissue implant of claim 13 wherein the passages allow said fluid filler to flow into and out of said cavity.

15. The tissue implant of claim 12 wherein said foam body is of a resilient material which is elastically deformable, the resiliency of said body enabling said body to deform in response to external pressure and to regain an original configuration following removal of such external pressure.

16. The tissue implant of claim 15 wherein, when an area of the implant is deformed by external pressure, the passages are configured to allow said fluid filler to flow from cells in the area of such deformation into other cells.

17. The tissue implant of claim 16 wherein, following the removal of such external pressure, the passages are configured to permit said fluid filler to equilibrate by returning to cells in the area where the deformation occurred.

18. The tissue implant of claim 11 wherein said shell is of a material which is substantially radiolucent under standard mammographic protocols and intensities.

19. The tissue implant of claim 18 wherein said shell is of a biocompatible material selected from the group consisting of linear aliphatic polyether urethane; linear aliphatic polyester urethane; cyclic aliphatic polyether urethane; cyclic aliphatic polyester urethane; aromatic polyether urethane; aromatic polyester urethane; polybutylene; polypropylene; crosslinked olefinic elastomers; and styrene-ethylene/butylene-styrene block copolymer.

20. The tissue implant of claim 11 wherein said fluid filler is of a biocompatible material which is substantially radiolucent under standard mammographic protocols and intensities.

21. The tissue implant of claim 20 wherein said fluid filler is a biocompatible triglyceride, serum, or saline solution.

22. The tissue implant of claim 11 wherein said foam body is of a material which is substantially radiolucent under standard mammographic protocols and intensities.

23. The tissue implant of claim 22 wherein said foam body is of a biocompatible material selected from the group consisting of styrene-ethylene-butylene-styrene copolymer; polyethylene; polyurethane; and polytetrafluoroethylene.

24. The tissue implant of claim 11 wherein each cell of the first multiplicity of cells is substantially of a first cell size and each cell of the second multiplicity of cells is substantially of a second cell size, the second cell size being different than the first cell size.

25. The tissue implant of claim 11 wherein said first foam region and said second foam region are each of a size sufficient to affect overall tactile characteristics of the implant.

26. The tissue implant of claim 11 wherein first and second cellular densities are sufficiently different from one another to affect overall tactile characteristics of the implant.

27. The tissue implant of claim 11 wherein the compound foam body consists solely of the first foam region and the second foam region.

* * * * *